(12) United States Patent
Abdulwahed et al.

(10) Patent No.: US 7,091,392 B2
(45) Date of Patent: Aug. 15, 2006

(54) DEHYDROGENATION PROCESS FOR OLEFINS

(75) Inventors: Mazhar Abdulwahed, Damascus (SY); Saeed M. Al-Zahrani, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 524 days.

(21) Appl. No.: 10/384,291

(22) Filed: Mar. 7, 2003

(65) Prior Publication Data

US 2004/0176657 A1    Sep. 9, 2004

(51) Int. Cl.
*C07C 5/333* (2006.01)
*C07C 5/373* (2006.01)

(52) U.S. Cl. .................... 585/662; 585/658
(58) Field of Classification Search ............... 585/658, 585/662
See application file for complete search history.

(56) References Cited

U.S. PATENT DOCUMENTS

| 3,697,614 | A | | 10/1972 | Tomezsko | 585/658 |
| 3,725,249 | A | | 4/1973 | Vesely | 208/139 |
| 4,046,833 | A | | 9/1977 | Hardman | 585/658 |
| 4,788,371 | A | | 11/1988 | Imai | 585/443 |
| 4,996,387 | A | | 2/1991 | Gerhold | 585/654 |
| 5,386,074 | A | * | 1/1995 | Durante et al. | 585/658 |

* cited by examiner

*Primary Examiner*—Walter D. Griffin
*Assistant Examiner*—In Suk Bullock
(74) *Attorney, Agent, or Firm*—Kramer Levin Naftalis & Frankel LLP

(57) ABSTRACT

A process for the dehydrogenation of alkane hydrocarbons is disclosed. The process comprises contacting an alkane with a chromium-based dehydrogenation catalyst in the presence of molecular oxygen at a temperature of from about 400° C. to about 700° C., a pressure of from about 0.1 to about 10 atmospheres, wherein the alkane to oxygen molar ratio is between about 1:0.0001 to 1:0.04.

17 Claims, 5 Drawing Sheets

Oxygen Concentration v. Isobutylene Yield

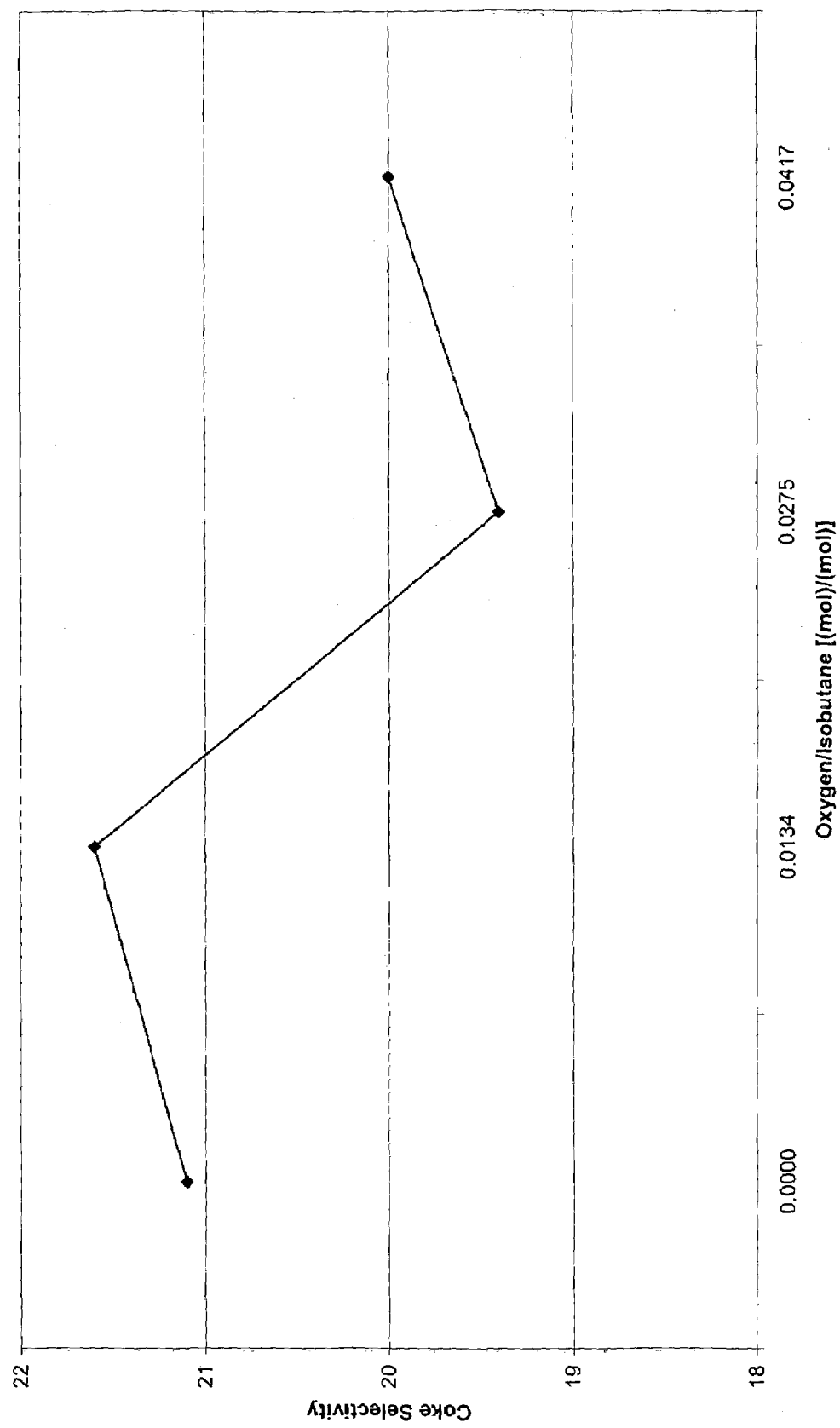

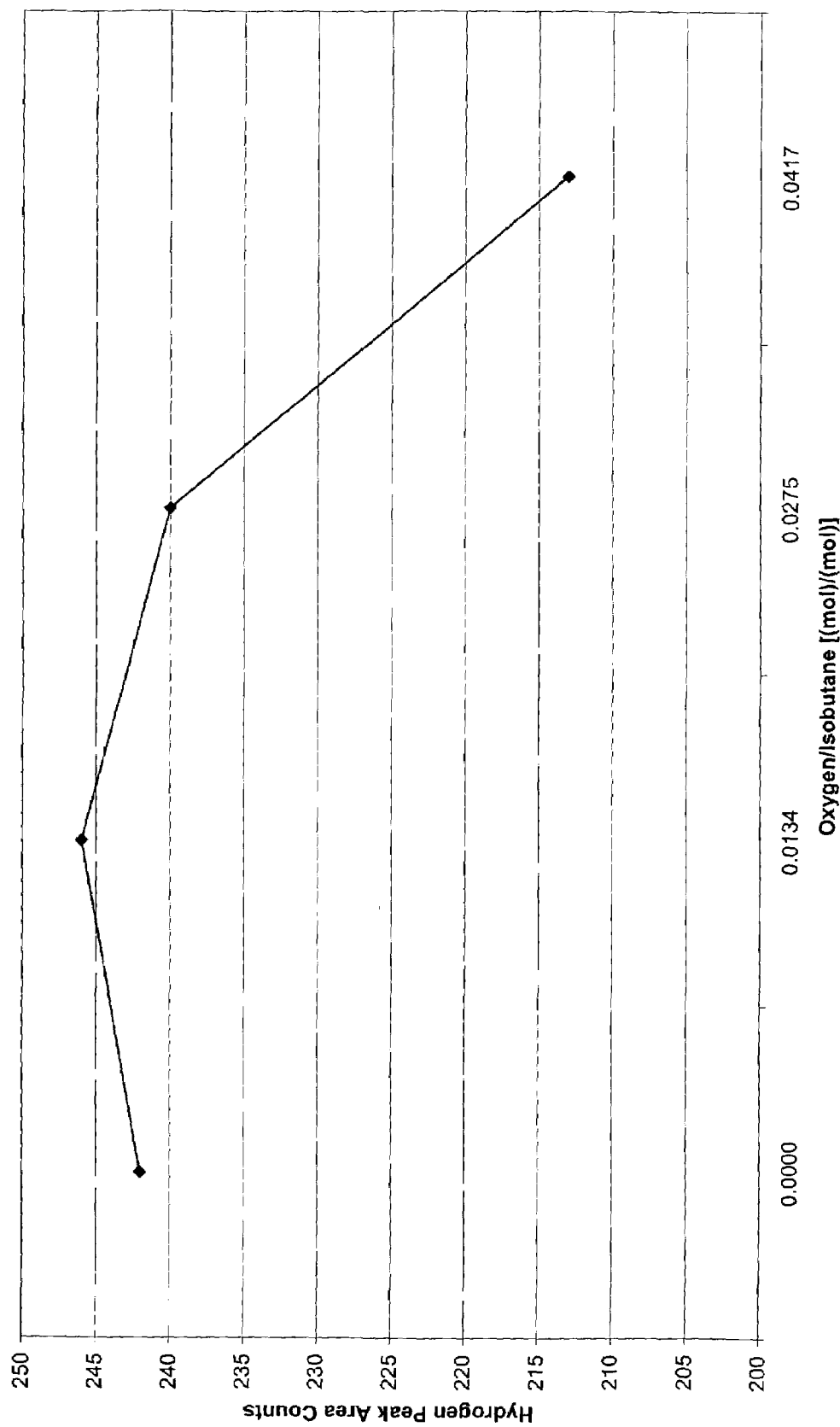

DEHYDROGENATION PROCESS FOR OLEFINS

FIELD OF THE INVENTION

This invention relates to a process for the production of olefin by normal dehydrogenation of corresponding paraffin. More particularly, this invention relates to an improved dehydrogenation process for olefin production employing chromium-based dehydrogenation catalysts in the presence oxygen.

BACKGROUND INFORMATION

The dehydrogenation of hydrocarbons is an important commercial process. This is because of the great demand for dehydrogenated hydrocarbons as feedstocks for industrial processes. For example, dehydrogenated hydrocarbons are utilized in the manufacture of detergents, high octane gasolines, pharmaceutical products, plastics and synthetic rubbers, among others. One example of a specific dehydrogenation process is dehydrogenating isobutane to produce isobutylene, which may then be polymerized to provide tackifying agents for adhesives, viscosity-index additives for motor oils and impact-resistant and anti-oxidant additives for plastics. Isobutylene may also used in the manufacture of Methyl Tertiary Butyl Ether (MTBE) or may be dimerized to isooctane. MTBE and isooctane are used as anti-knocking agents in gasoline fuels.

The major traditional sources of alkenes have been steam cracking, and fluid catalytic cracking. Both processes simultaneously provide a wide range of other products with limited flexibility. However, the demand is growing for specific alkenes, such as isobutylene or propylene, and it is not cost effective to satisfy that demand utilizing expensive cracking units. The best technical choice for providing alkenes has been normal dehydrogenation of alkanes.

Major factors affecting the technical implementation of the alkane dehydrogenation are the thermodynamic equilibrium limiting single pass conversion and the endothermic character of the dehydrogenation reaction. Additionally, the temperature required for conventional dehydrogenation causes thermal cracking which lowers alkene selectivity, especially in case of propane dehydrogenation.

Two types of catalysts based on chromium oxides for the dehydrogenation of lower alkanes have been described in the scientific and patent literature: chromium oxides supported on $\gamma,\delta/,\theta$-alumina doped with alkali metal and chromium oxides supported on $ZrO_2$. Chromium oxides supported on $\gamma,\delta/,\theta$-alumina doped with alkali metal is employed in the Lumnus Catofin and Snamprogetti-Yarsintez fluidized bed dehydrogenation processes. Chromium oxides supported on $ZrO_2$, on the other hand, has been investigated for its higher thermal stability relative to alumina.

The nature of the active sites in chromium oxide-supported catalysts has been debated for many years. $Cr_2O_3$ is the most stable form of all the possible chromium oxides.

Two types of $Cr^{6+}$ species have been detected in chromium oxide supported on alumina, after the calcination treatment and before reaction. After reduction with hydrogen, it is generally believed that all $Cr^{6+}$ is reduced to $Cr^{3+}$. However, according to Grunert et al. (J. Catal. 110 (1986), 138), the reduction occurs in two steps: a very rapid steps from $Cr^{6+}$ to $Cr^{3+}$, followed by a slower step from $Cr^{3+}$ to lower oxidation states ($Cr^{2+}$). The active sites of the dehydrogenation reactions have been assumed to be $Cr^{3+}$ by Grunert, W. et al. (J. Catal. 99 (1986), 149; Delmon, B. et al. (J. Catal. 24 (1972), 336) and Konig, P. et al. (Acta Chim. Acad. Sci. Hung. 76 (1976), 123), and to be both $Cr^{2+}$ and $Cr^{3+}$ by Ashmawy, F. M. (J. Chem. Soc., Faraday Trans. 76 (1980), 2096), or coordinatively unsaturated $Cr^{2+}$ by Lunsford, H. et al. (J. Catal. 91 (1985), 155).

The activity in the dehydrogenation of isobutane and also of ethane has been found to be proportional to the chromium content, whatever the species present. Also, in the case of propane dehydrogenation over $ZrO_2$ supported chromium oxide (Indovina et al., Appl. Catal. 81 (1992), 113), the activity per atom of chromium was found to be the same for all chromium loadings. The activity was attributed to the presence of mononuclear $Cr^{3+}$ species.

However, since hydrogen is present as part of the dehydrogenation reaction product, further reduction of $Cr^{3+}$ will continue. It is shown in this invention that the lower oxidation state chromium species are responsible for undesired cracking reactions taking place during dehydrogenation and thus to be responsible for coke formation. To minimize the formation of cracking products and coke, the oxidation state of chromium catalytic sites must be controlled by means of a functional redox system during the reaction cycle. The redox system according to present invention is believed to be $Cr^{2+}/Cr^{3+}/O_2$, as demonstrated by oxygen addition to the hydrocarbon in the feed.

It is known from the literature that oxygen can shift the thermodynamic equilibrium of dehydrogenation reactions towards increased olefin production by reacting with hydrogen product. Oxygen is also believed to combust coke and thereby keep the catalyst surface clean of coke deposits. Regeneration of the catalyst is thereby avoided, since coke does not build up and consequently the catalyst is not deactivated. Such reactions are called oxidative dehydrogenation reactions. Up to date there is no commercial process available for producing light alkanes, especially $C_3$ and $C_4$-olefins, by oxidative dehydrogenation reactions due to the absence of a proper catalyst. Known oxidative dehydrogenation reaction processes are described in several published patents.

For example, U.S. Pat. No. 4,996,387 disclosed a dehydrogenation process with a continuous regeneration of dehydrogenation catalyst achieved by cyclically contacting a portion of the catalyst with an admixture of oxygen containing regeneration gas and diluent, while contacting the remaining portion of the catalyst with an admixture of hydrocarbon feed material and diluent. In this disclosure oxygen is added for the purpose of catalyst regeneration in a separate regime from the dehydrogenation medium.

Canadian Patent 912,051 describes a vapor phase process for dehydrogenation of paraffin and olefins with oxygen and halogen in the presence of a solid catalyst containing an alkali metal or an alkaline earth metal compound and a promoter. U.S. Pat. No. 3,697,614 is directed to olefin production by oxidative dehydrogenation using a molten alkali metal hydroxide containing alumina with solution transition metal oxygenation, preferably consisting of dichromate molybdate, tungstate, manganate, permanganate, ferrate and metavanadate.

U.S. Pat. No. 4,046,833 disclosed a vapor phase process for dehydrogenation of paraffinic hydrocarbon containing 3 to 6 carbon atoms to the corresponding monoolefin, wherein the process is carried out in the presence of oxygen and in the presence of an oxidative dehydrogenation catalyst containing vanadium and aluminum. The effective paraffin to oxygen ratio is claimed to be in the range of 1:0.04 to 1:10. Examples given in the mentioned invention demonstrate only the effect of several catalyst compositions tested under different conditions with different oxygen concentrations.

U.S. Pat. No. 4,788,371 discloses another oxidative dehydrogenation process using a dehydrogenation catalyst comprising at least one noble metal component. According to the low olefin selectivity, and to date are not utilized on any commercial scale due to absence of a suitably active and selective catalyst, and because the concentration oxygen heretofore utilized in such processes has not been in accord with this invention.

In the production of olefins by the catalytic dehydrogenation of paraffin, it is, of course, desirable to obtain as high a yield of olefin as is possible in a single conversion pass. To minimize hot spot effects, and consequently increase the life of the catalyst, it is also desirable to conduct the reaction under such conditions wherein a minimum amount of coke is formed on the catalyst. It is also desired to increase the dehydrogenation reaction period by decreasing coke formation.

The advantage of the present invention is the maintaining of high paraffin conversion while increasing olefin yield and selectivity, the reduction of thermal cracking, decreasing the feedstock consumption and extending catalyst life.

SUMMARY OF THE INVENTION

It is an object of the invention to provide a dehydrogenation process for the production of olefins which provides high alkane conversion and increased olefin selectivity.

It is another object of the invention to provide a process for hydrocarbon dehydrogenation for the production of olefins with high yield, less feedstock consumption and less coke formation.

It is another object of the present invention to extend dehydrogenation reaction cycle time.

Other objects and advantages of the invention will be apparent from the following description. disclosure, an alkane feed including an oxygen containing gas is introduced into a dehydrogenation reactor containing the noble metal catalyst. The oxygen added to the reactor feed is in a molar ratio to alkane which is very similar to that of U.S. Pat. No. 4,046,833 (and different from the ratio used in the present invention as shall be described below). The effect of oxygen on the described system is to combust hydrogen while minimizing the combustion of valuable hydrocarbons.

Numerous processes have also been disclosed which involve the removal of hydrogen from a mixture of hydrogen and one or more organic compounds: For example, U.S. Pat. No. 4,788,371, as well as other patents referenced therein, disclose a process for the dehydrogenation of hydrocarbons in which hydrogen obtained by such hydrocarbon dehydrogenation is catalytically reacted with oxygen. A disadvantage of all of these processes is that some of the oxygen gas reacts chemically with the organic compounds instead of with just the hydrogen, thus converting them into undesired products.

European Patents A1-0219271 and A1-0219272 also disclose processes for the dehydrogenation of hydrocarbons in which hydrogen obtained by the dehydrogenation of the hydrocarbons is removed. In these processes, the dehydrogenation takes place in the presence of a zeolite catalyst, and the hydrogen is removed by chemical reaction with an acidic oxide such as sulfur dioxide or nitrous oxide. These processes do not share the disadvantage of processes which utilize oxygen gas, because sulfur dioxide and nitrous oxide are not as reactive as is oxygen towards organic compounds. These processes also appear to be less effective in the removal of hydrogen.

The oxidative dehydrogenation reaction processes described above are totally different from the process of the present invention as described below. They generally suffer The present invention provides an improved process for the production of olefin by normal dehydrogenation of corresponding alkane, and especially for the improved dehydrogenation of hydrocarbons on chromium-based dehydrogenation catalysts using oxygen. The chromium-based dehydrogenation catalyst useful in the instant process has been found to be surprisingly selective towards the oxidation of hydrogen in the presence of small amounts of oxygen, resulting in an increase in the yield of the desired dehydrogenated product. Accordingly, the process of the present invention is broadly directed to a hydrocarbon conversion process, and specifically towards a process of dehydrogenation of hydrocarbons on chromium-based dehydrogenation catalysts using small amounts of oxygen.

The hydrocarbon dehydrogenation process of the invention utilizes a dehydrogenation catalyst comprising 10–20% by weight of chromium to promote dehydrogenation of a feedstock comprising dehydrogenatable hydrocarbon and a small amount of pure oxygen, wherein the hydrocarbon to oxygen molar ratio should be between about 1:0.0001 and 1:0.04. According to an example of the preferred embodiment of the invention, the dehydrogenatable hydrocarbon is isobutane, the oxygen is provided in an amount between 0.0001 to 0.001 gram mole oxygen per gram chromium in the catalyst and reaction temperature being between 560° C. to 600° C.

In a further example of an embodiment of the present invention, air or other oxygen-containing gas is used in place of pure oxygen.

BRIEF DESCRIPTION OF THE DRAWINGS

FIG. 4 is a graph depicting coke selectivity as a function of oxygen concentration in the process of the present invention; and FIG. 5 is a graph depicting hydrogen peak area count as a function of oxygen concentration in the process of the present invention.

DETAILED DESCRIPTION OF THE INVENTION

Figure 1:
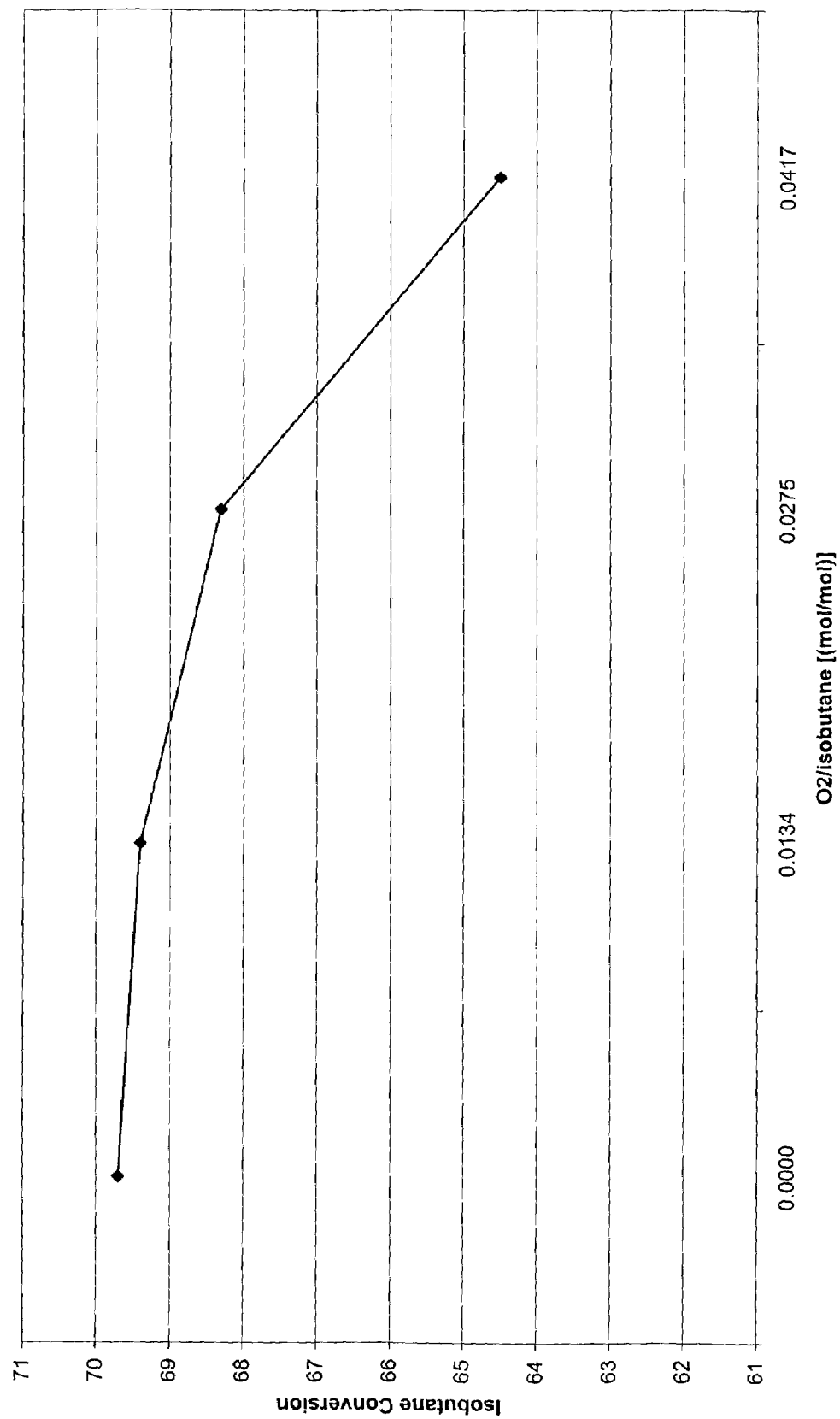
FIG. 1 is a graph depicting isobutane conversion as a function of oxygen concentration in the process of the invention.

The present invention relates to an improved process for the production of olefin, and particularly isobutylene, by normal dehydrogenation of corresponding paraffin. The process is aimed at minimizing the side reactions occurring during the dehydrogenation reaction by controlling the oxidation state of chromium sites in the dehydrogenation catalyst. This is achieved by the addition of small amounts of oxygen. The oxygen addition according to the invention provides an in situ heat source for the reaction, decreases coke formation, enhances olefin selectivity and extends the dehydrogenation catalytic cycle. In another embodiment of the invention, air or oxygen-containing gas may be used in place of oxygen.

The dehydrogenation catalyst useful in this invention comprises 10–20% by weight of chromium, and preferably, 12–18% by weight of chromium. The chromium-based dehydrogenation catalyst may be spray dried, pelletized or shaped, preferably it is spray dried. The catalyst used in the instant process may be used alone, or supported on or impregnated in a carrier material. Suitable carrier materials include alumina, silica, thoria, zirconia, titania, boron phosphate, silicon carbide, pumice, diatomaceous earth, clay, and the like. The catalysts of the invention are preferably calcined to produce desirable physical properties such as attrition resistance, optimum surface area and particle size.

The dehydrogenation of a dehydrogenatable paraffinic hydrocarbon, such as isobutane, is effected in the instant process by contacting the dehydrogenatable paraffinic hydrocarbon, with the previously described catalyst at conditions suitable for normal dehydrogenation. Such conditions comprise temperatures which range from about 400° C. to about 700° C., preferably, between about 500° C. to about 650° C. and, more preferably, between about 560° C. to about 600° C., and a reaction pressure in the range of from about 0.1 to about 10 atmospheres.

Oxygen concentration in the process of the present invention is critical to obtain the described benefits of the invention. In one embodiment, required oxygen amount for isobutane dehydrogenation is between 0.0001 to 0.001 gram mole oxygen per gram chromium in the catalyst, preferably, between 0.0002 to 0.0008 gram mole oxygen per gram chromium in the catalyst. In addition, the molar ratio of dehydrogenatable hydrocarbon to oxygen is desirably between 1:0.0001 to 1:0.04, preferably, between 1:0.001 to 1:0.04, and more preferably, between 1:0.01 to 1:0.035.

Oxygen may be added to the instant process in various ways such as by admixing oxygen with a relatively cool alkane hydrocarbon feed stream or with a steam diluent, or it may be added directly to the reactor independently of the feed alkane hydrocarbons.

Inert diluent may be employed in the dehydrogenation process of this invention. Any inert material, which will not adversely affect the dehydrogenation process, may be employed as diluent. Examples of suitable diluents are methane, ethane, propane, nitrogen, or steam.

The process of the invention can be applied to any dehydrogenatable paraffinic hydrocarbon and in any type of dehydrogenation reactor, including fixed bed, moving bed and fluidized bed. Preferred embodiments of the invention utilized a fixed bed catalytic system or a dense phase moving bed system, such as is shown in U.S. Pat. No. 3,725,249.

One fixed bed catalytic reaction system for the present invention is comprised of a single reaction zone within a single reactor with single inlet to the reactor and with the products and by-products of the process exiting through a reactor outlet port.

In another embodiment of the invention, a fix bed catalyst system has multiple oxygen inlet ports separate along the reaction zone so that oxygen can be injected at different points into the catalyst bed of the reaction zone. This type of configuration mimics a reaction system with a plurality of catalyst beds.

In an alternative embodiment, the process of the instant invention is accomplished in a moving bed catalytic system, such as the system described in U.S. Pat. No. 3,725,249. This embodiment of the invention is most useful for use for reactions where the catalyst is known to be deactivated by coke deposition thereon. In this embodiment, the catalyst of the instant process continuously moves through the plurality of reaction zones of the process and, once deactivated, is transported to a continuous catalyst regeneration system. Once regenerated, the catalyst is returned to the reaction system.

EXAMPLES

The invention will now be more fully described and understood with reference to Example 1 through 9. These examples are given by way of illustration and the claimed invention is not limited by these examples.

The catalyst used in the following examples is a commercially available chromium-alumina based dehydrogenation catalyst containing 14% chromium and manufactured by spray dryer method (catalyst T-2715 from United Catalyst, Inc.).

Five or one gram of the catalyst was loaded in a standard SS fixed bed reactor constructed of a 1-inch tube. A ⅛ inch thermowell was located axially in the reactor tube to enable temperature measurement. The reactor was placed in an oven heated electrically for maintaining the desired temperature. The reactor effluent was directed to an on-line connected GC HP 6890 provided with FID and TCD detectors. Nitrogen was introduced into the reactor effluent at constant rate to provide an internal standard for accurately calculating the mass balance. The catalyst was pre-treated with 33.3 cc/min helium at the reaction temperature for five (5) minutes before introduction of the feed at the given composition into the reactor. Analysis of the reactor products were taken and reported in Tables 1 and 2. After analysis of the reaction product, the reaction was stopped, the catalyst flushed with nitrogen and then regenerated using an oxygen flow of 33.3 cc/min at the same reaction temperature. The catalyst pretreatment can be with hydrogen, nitrogen or methane. The purpose of catalyst pretreatment is to reduce the catalyst and make it ready for reaction. Regeneration with oxygen is not limiting and it can be carried out using air.

The percent conversion obtained as shown in the below Tables represents the total isobutane converted to isobutylene and other products. The selectivity to isobutylene reported is the percent of isobutylene obtained based on isobutane converted, all percents being calculated on a molar basis. Productivity (Prod·$g_{HC}^=/g_{cat}·h$) is defined as grams of isobutylene ($_{HC}^=$) produced per gram of catalyst, per hour. Feedstock consumption (Cons·$g_{HC}/g_{cat}·h$) is defined as grams of isobutane consumed per gram, per hour. W/F is defined as weight of the catalyst in gram divided by the flow rate of reactant stream in ml/sec measured at S.T.P.

In Table 1, experimental conditions carried out on isobutane dehydrogenation are given. All examples in Table 4 were carried out on 5 gm of the catalyst. Example 1 to 6 were conducted at 580° C., and examples 7 to 9 were conducted at 575° C. and using 25 ml/min isobutane without oxygen addition. Reaction temperature was 580° C. Results are given in Table 2. Reported results represent catalyst activity measured after 5 minutes of reaction except for Examples 2 and 5 which were measured after 10 minutes of reaction. In Table 2, X stands for conversion; S stands for selectivity; Y stands for yield in mol %; $iC_4$ stands for isobutane; $iC_4^=$ stands for isobutylene, and $H_2$ Area stands for hydrogen peak area count.

TABLE 1

Isobutane Dehydrogenation Conditions for Examples 1–9

| Example # | W/F [$g_{cat} \cdot sec/ml$] | $O_2$/isobutane [mol/mol] | Reaction time [min] |
|---|---|---|---|
| 1 | 12 | 0 | 5 |
| 2 | 12 | 0 | 10 |
| 3 | 12 | 0.0134 | 5 |
| 4 | 12 | 0.0275 | 5 |
| 5 | 12 | 0.0275 | 10 |
| 6 | 12 | 0.0417 | 5 |
| 7 | 4 | 0 | 5 |
| 8 | 4 | 0.0135 | 5 |
| 9 | 4 | 0.0274 | 5 |

TABLE 2

Isobutane Dehydrogenation Results

| Ex. # | $O_2$/Cr (content in catalyst) [$g \cdot molO_2/g_{Cr}$] | X, $iC_4$ | S, $iC_4=$ | Y, $iC_4=$ | S, Coke | $H_2$, Area | Prod · $g_{C4}$ = / $g_{cat} \cdot h$ | Cons · $g_{C4}$/ $g_{cat} \cdot h$ |
|---|---|---|---|---|---|---|---|---|
| 1 | 0 | 69.7 | 70.2 | 48.9 | 21.1 | 242 | 0.39 | 0.58 |
| 2 | 0 | 72.7 | 56.6 | 41.2 | 31.4 | 274 | 0.33 | 0.61 |
| 3 | 0.00034 | 69.4 | 71.2 | 49.4 | 21.6 | 246 | 0.39 | 0.57 |
| 4 | 0.00068 | 68.3 | 73.6 | 50.3 | 19.4 | 240 | 0.39 | 0.55 |
| 5 | 0.00068 | 69.4 | 67.0 | 46.5 | 27.4 | 276 | 0.36 | 0.56 |
| 6 | 0.00102 | 64.5 | 73.1 | 47.2 | 20.0 | 213 | 0.36 | 0.52 |
| 7 | 0 | 58.2 | 55.6 | 32.3 | 41.7 | 409 | 0.78 | 1.45 |
| 8 | 0.00102 | 46.7 | 63.9 | 30.0 | 33.9 | 231 | 0.71 | 1.15 |
| 9 | 0.00204 | 27.4 | 60.3 | 16.6 | 34.1 | 140 | 0.39 | 0.67 |

Figure 2:
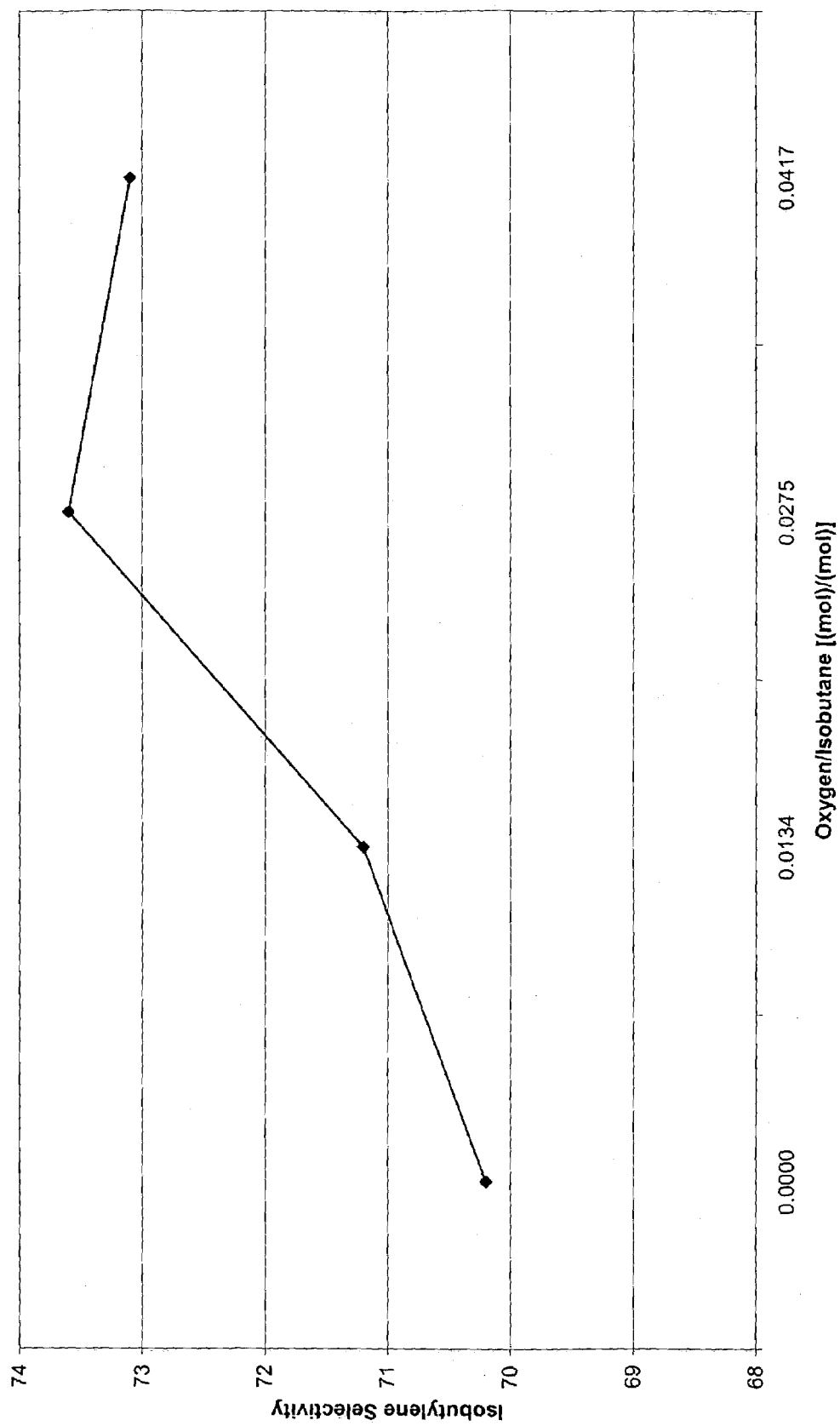
FIG. 2 is a graph depicting isobutylene selectivity as a function of oxygen concentration in the process of the present invention.
Figure 3:
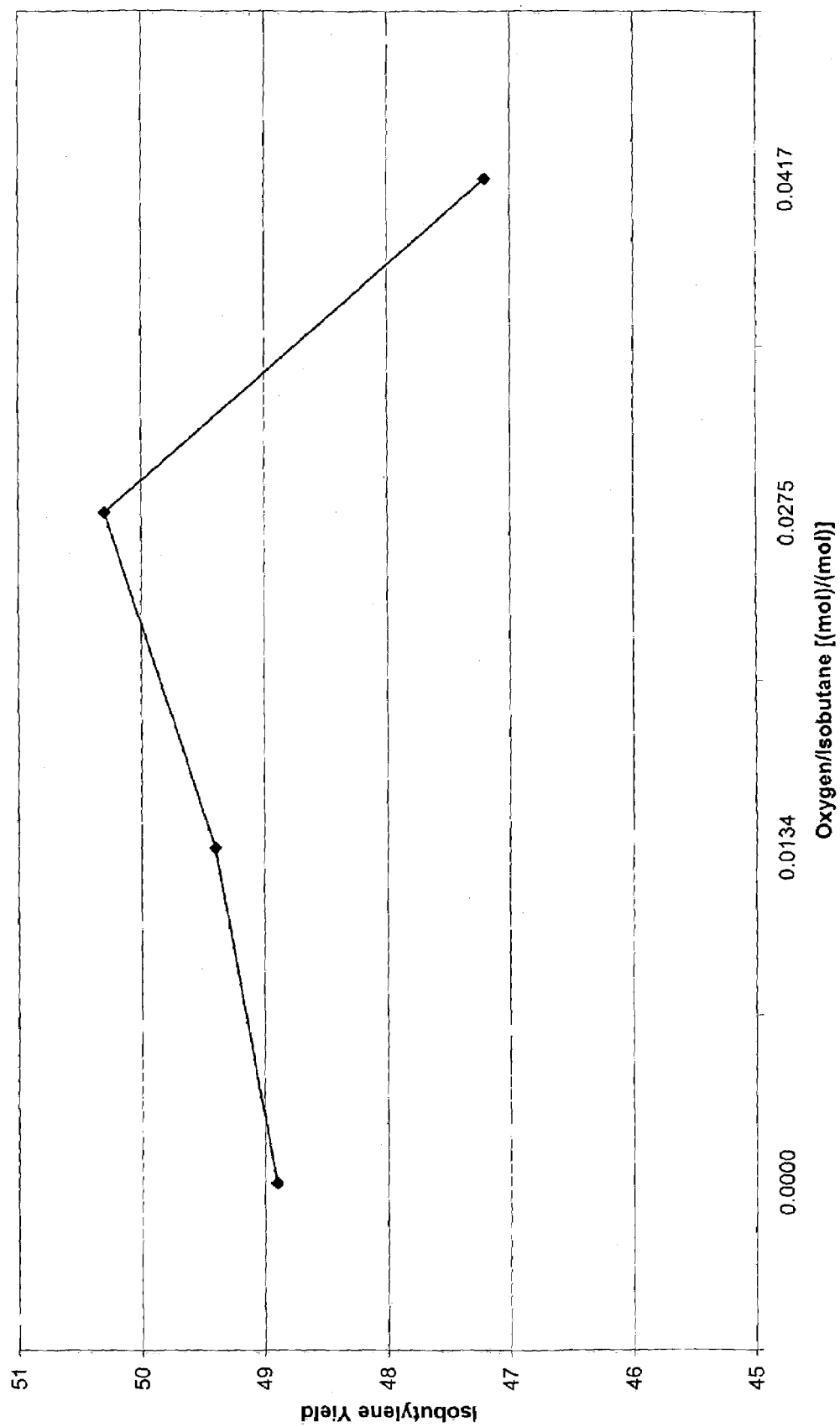
FIG. 3 is a graph depicting isobutylene yield as a function of oxygen concentration in the process of the present invention.

Results for Examples 1, 3, 4 and 6 were selected and graphed in FIGS. 1 through 5. From FIGS. 1, 2 and 3, it can be seen that isobutane conversion drops while isobutylene selectivity and yield increases as the ratio of oxygen to isobutane in the feed increases to a maximum at a $O_2$/isobutane molar ratio of 0.0275. Further increase in oxygen concentration results in decreases in both conversion and selectivity. This result is very important, since operating at the prescribed $O_2$ concentration yields an approximate 5% savings of the hydrocarbon feedstock, isobutane. In addition, oxygen addition according to the invention enables continued isobutane saving and more isobutylene productivity at longer reaction times (Examples 2 and 5), and due to less coke formation, it allows an extended reaction time.

FIG. 4 shows that lowest coke selectivity occurs at $O_2$/isobutane molar ratio of about 0.0275. Higher or lower $O_2$/isobutane molar ratio would likely result a higher coke selectivity. FIG. 5 shows hydrogen peak area given for Examples 1, 3 and 4 (or in examples 2 and 5) are almost the same regardless of oxygen amounts in the range where oxygen promotes olefin formation. The hydrogen peak area decreases when additional oxygen is added and both isobutane conversion and isobutylene selectivity drop (see Example 6). Further addition of oxygen shift the reaction to the product side as expected according to reaction equilibrium.

The Examples clearly demonstrate the function of oxygen as a selective controller of chromium redox properties. It is shown that the oxidation of chromium by oxygen molecules proceeds much faster than the oxidation of hydrogen or coke active species at the catalyst surface.

Operation of isobutane dehydrogenation at lower W/F ratio is not attractive, as it can be seen from productivity and feed consumption rate figures in Examples 7, 8 and 9, even when the process of the invention is utilized.

Having thus described in detail preferred embodiments of the present invention, it is to be understood that the invention defined by the appended claims is not limited to particular details set forth in this description as many variations thereof are possible without departing from the spirit or scope of the present invention.

What is claimed is:

1. A process for alkane dehydrogenation comprising contacting an alkane with a chromium-based dehydrogenation catalyst which comprises 10% to 20% by weight chromium in the presence of molecular oxygen at a temperature of from about 400° C. to 700° C., a pressure of from about 0.1 to about 10 atmospheres, wherein the molar ratio of alkane to oxygen is about 1:0.0001 to 1:0.04.

2. The process of claim 1, wherein said alkane is isobutane.

3. The process of claim 1, wherein said catalyst comprises 12–18% of chromium by weight.

4. The process of claim 3, wherein the alkane is isobutane and the temperature is from about 500° C. to about 650° C.

5. The process of claim 3, wherein the alkane is isobutane and the temperature is from about 560° C. to about 600° C.

6. The process of claim 1, wherein the alkane dehydrogenation is performed over a fixed bed catalyst, a moving bed catalyst or a fluidized bed catalyst.

7. The process of claim 1, wherein said contacting is in the presence of an inert diluent.

8. The process of claim 7, wherein the alkane is isobutane and the inert diluent comprises methane, ethane, propane, nitrogen, or steam.

9. The process of claim 4, wherein said contacting is in the presence of methane, ethane, propane, nitrogen or steam.

10. The process of claim 5, wherein said contacting is in the presence of methane, ethane, propane, nitrogen or steam.

11. The process of claim 1, wherein the alkane to oxygen molar ratio is between about 1:0.001 to 1:0.04.

12. The process of claim 1, wherein the alkane to oxygen molar ratio is between about 1:0.01 to 1:0.035.

13. The process of claim 4, wherein the alkane to oxygen molar ratio is between about 1:0.01 to 1:0.035.

14. The process of claim 3, wherein the amount of oxygen present in relation to the amount of chromium in said catalyst is about 0.0001 to 0.001 gram mole of oxygen per gram chromium in the catalyst.

15. The process of claim 4, wherein the amount of oxygen present in relation to the amount of chromium in said catalyst is about 0.0002 and 0.0008 gram mole of oxygen per gram chromium in the catalyst.

16. The process of claim 5, wherein the amount of oxygen present in relation to the amount of chromium in said catalyst is about 0.0001 to 0.001 gram mole of oxygen per gram chromium in the catalyst.

17. The process of claim 12, wherein the amount of oxygen present in relation to the amount of chromium in said catalyst is about 0.0001 to 0.001 gram mole of oxygen per gram chromium in the catalyst.

\* \* \* \* \*